United States Patent [19]

Guillon et al.

[11]  4,438,140
[45]  Mar. 20, 1984

[54] SALTS OF ACID DYES AND COPOLYMERS HAVING TERTIARY AMINE FUNCTIONS, PROCESS FOR PREPARING SAID SALTS AND MAKEUP COSMETIC COMPOSITIONS CONTAINING THEM

[75] Inventors: Michel Guillon, Bourg-La-Reine; Jean Mondet, Sevran; Christos Papantoniou, Montmorency; Claudine Vandenbossche, Aulnay-Sous-Bois, all of France

[73] Assignee: Societe Anonyme Dite: L'Oreal, Paris, France

[21] Appl. No.: 252,809

[22] Filed: Apr. 10, 1981

[30] Foreign Application Priority Data

Apr. 18, 1980 [FR] France ............................... 80 08742

[51] Int. Cl.³ .................... A61K 7/04; A61K 7/021
[52] U.S. Cl. ................ 424/61; 424/DIG. 5; 424/63; 424/64; 424/69; 424/168; 424/358; 424/365; 525/375; 525/376; 525/153; 525/348; 525/385; 525/326.9

[58] Field of Search .............. 424/61, DIG. 5, 63, 424/64, 69; 260/328.5

[56] References Cited

U.S. PATENT DOCUMENTS

| | | | |
|---|---|---|---|
| 3,849,547 | 11/1974 | Kalopissis | 424/61 |
| 3,911,105 | 10/1975 | Papantoniou et al. | 526/328.5 |
| 3,966,574 | 6/1976 | La Bash et al. | 526/328.5 |
| 4,064,161 | 12/1977 | Lewis et al. | 526/328.5 |

FOREIGN PATENT DOCUMENTS

| | | | |
|---|---|---|---|
| 2105972 | 4/1972 | France | 424/81 |
| 435494 | 10/1960 | Switzerland | 424/78 |
| 726116 | 4/1980 | U.S.S.R. | 526/326.5 |

*Primary Examiner*—Dale R. Ore
*Attorney, Agent, or Firm*—Cushman, Darby & Cushman

[57] ABSTRACT

The present invention concerns new acid colorant and copolymer salts carrying tertiary amine functions, the process for preparing said salts, as well as the makeup compositions and in particular the lipsticks and nail varnishes containing as coloring substances the saits according to the invention.

16 Claims, No Drawings

SALTS OF ACID DYES AND COPOLYMERS HAVING TERTIARY AMINE FUNCTIONS, PROCESS FOR PREPARING SAID SALTS AND MAKEUP COSMETIC COMPOSITIONS CONTAINING THEM

The present invention concerns new acid colorant and copolymer salts carrying tertiary amine functions, the process for preparing said salts, as well as the makeup compositions and in particular the lipsticks and nail varnishes containing as coloring substances the salts according to the invention.

Makeup products represent a nonnegligeable share of the so-called cosmetic products but are very often subject to variations in fashion.

This is most particularly the case with lipsticks and nail varnishes which in the last few years have come back into vogue.

Despite the many improvements made in these makeup products in order to remedy some of their drawbacks, there still remains one which has considerably hindered their development; this is essentially the phenomenon known to cosmeticians by the name of "hold."

These products in fact contain coloring substances which tend to superficially color the skin, the mucous membranes, and the nail keratin.

"Hold" is thus the color-prone tendency of a given coloring substance, and we therefore conceive the need to diminish its effects so that this coloring remains sufficiently weak and is as invisible as possible after makeup removal. This is most particularly true for lipsticks which, when they are applied beyond the mucous membranes of the lips or when they "migrate," may leave stains on the mucous membrane or the periphery of the lips, thus unesthetically modifying their contour.

Various means have been proposed for remedying this major drawback of makeup products, without however any satisfactory solutions having been reached.

In French Pat. No. 1.588.210 there has been proposed the use in lipsticks of bromacid colorant salts and certain amine salts such as diethanolamine, triethanolamine, amino-2 methyl-2, propanediol-1,3, mono-isopropanolamine, morpholine and diglycolamine.

However, such salts have not made it possible to satisfactorily solve the problem posed by "hold."

After new research in this field, it has now been found that excellent results can be obtained if special copolymers carrying tertiary amine functions are used, and more particularly copolymers having patterns carrying N,N-dialkylaminoalkyl functions are used for the salification of the special copolymers.

The tests done have in fact made it possible to show that by using these acid colorant and amino copolymer salts it is possible to reduce or even eliminate altogether the "hold" effect caused by the use of these colorants in makeup compositions, such as lipsticks, nail varnishes, rouges or eye shadows, foundations and mascaras.

Furthermore, it has been found that by using such salts it is possible to achieve excellent dispersions of the coloring substances in the body of makeup products so that no inequality of manufacture results which might show up as variations in hue.

Finally, no alteration of the coloration in time has been noted, the coloration of the makeup product being virtually identical to the color conferred on the epidermis or the nail keratin.

The present invention concerns new acid colorant salts, and in particular halogeno-acid, azoic, anthraquinonic and other colorants carrying at least one acid function, said salts resulting from salification of said acid colorants by a copolymer carrying tertiary amine functions corresponding to the following formula:

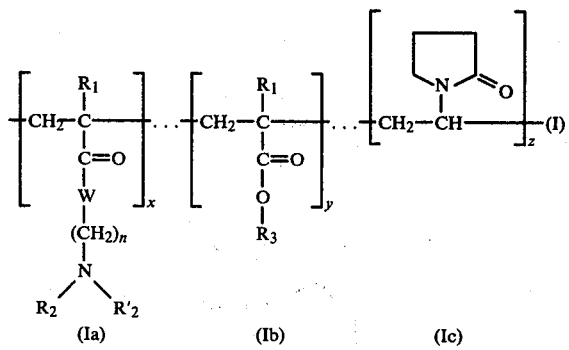

in which:

n is 2 or 3,

W represents a bond, —O— or —NH—, $R_1$ represents H or —$CH_3$, $R_2$ and $R'_2$, identical or different, represent a lower alkyl radical having from 1 to 3 atoms of carbon, $R_3$ represents a linear or branched alkyl radical having from 1 to 18 carbon atoms, x represents from 5 to 95% by weight, preferably 15 to 75%, y represents from 5 to 95% by weight, preferably 25 to 85%, and z represents from 0 to 20% by weight, $x+y+z$ being equal to 100%.

Among the various acid colorants which can be salified, the following may in particular be cited:

(1) halogeno-acid colorants known under the respective names of "Red 21 D and C," "Orange 5 D and C," "Red 27 D and C," "Orange 10 D and C," and "Red 3 D and C," these colorants corresponding to the following formulas:

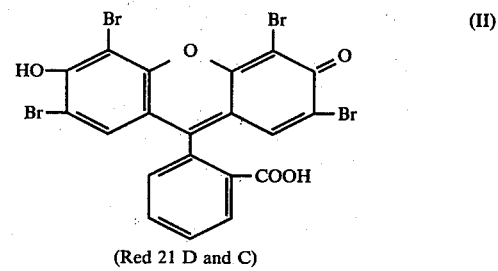

(Red 21 D and C)

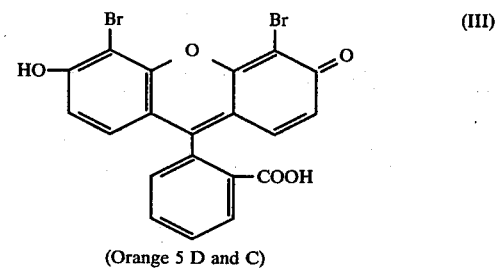

(Orange 5 D and C)

-continued

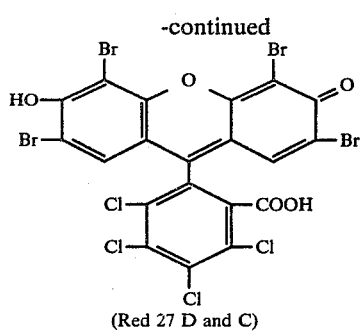
(Red 27 D and C)

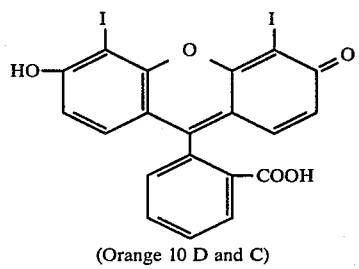
(Orange 10 D and C)

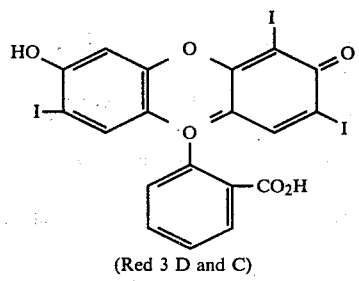
(Red 3 D and C)

(2) The acid colorants of the azoic series, and in particular those corresponding to the following formulas:

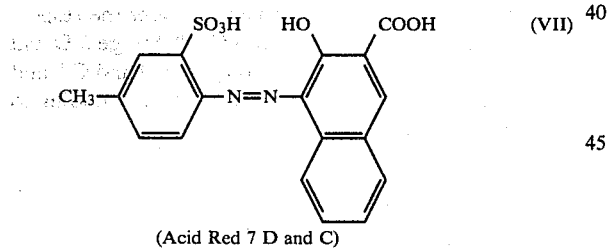
(Acid Red 7 D and C)

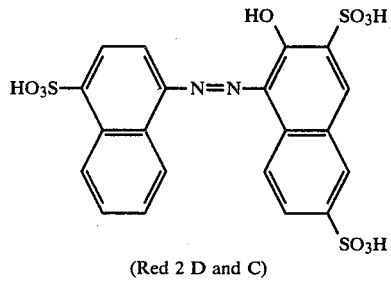
(Red 2 D and C)

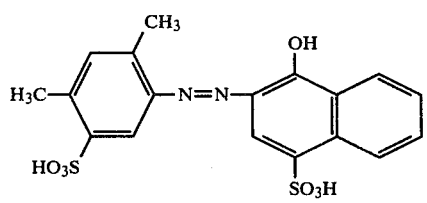

-continued
(Red 4 D and C)

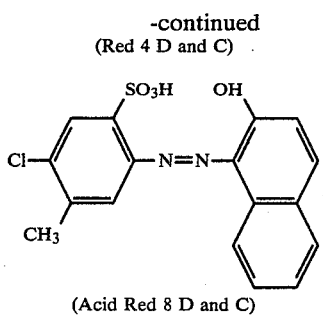
(Acid Red 8 D and C)

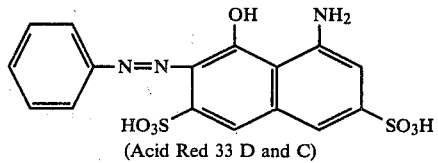
(Acid Red 33 D and C)

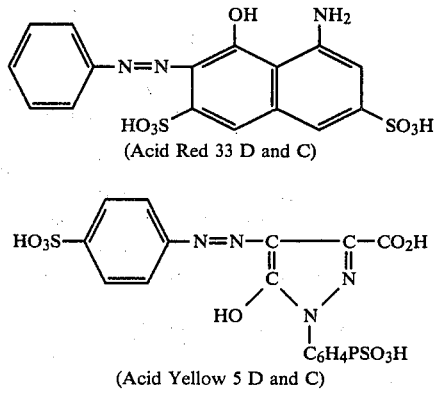
(Acid Yellow 5 D and C)

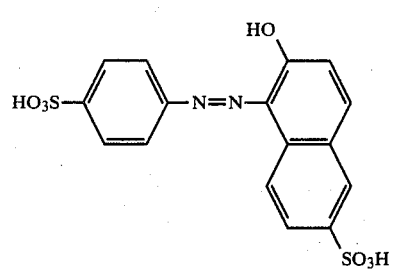
(Acid Yellow 6 D and C)

(3) The colorants of the anthaquinonic series, in particular the colorant corresponding to the following formula:

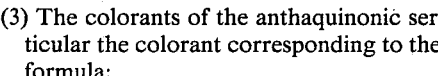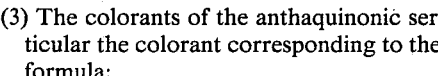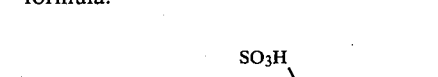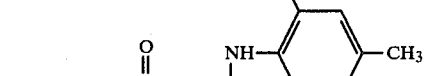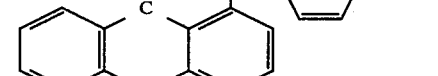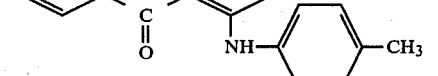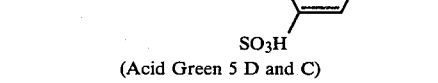
(Acid Green 5 D and C)

and (4) Those acid colorants having diverse structures, among which may be cited (Acid) Yellow 10 D and C, (Acid) Green 3 D and C, Blue 1 D and C, Blue 2 D and C, and Violet 1, D and C, this enumeration not being limiting.

The copolymers of formula (I) as defined above serving to salify the acid colorants are for the most part well known and are obtained by polymerization of at least two monomers, one of which has a tertiary amine function and the other is an acrylate or alkyl methacrylate.

Among the monomers able to lead to the patterns of formula (Ia), we may cite: the acrylates and methacrylates of ethyl N,N-dimethylamino-2, ethyl N,N diethylamino-2, propyl N,N-dimethylamino-3, propyl N,N-diethylamino-3, and the acrylamides and methacrylamides of ethyl N,N-dimethylamino-2, ethyl N,N-diethylamino-2, propyl N,N-dimethylamino-3, and propyl N,N-diethylamino-3.

Among the monomers able to lead to the patterns in formula (Ib) we may cite the acrylates and methacrylates of methyl, ethyl, propyl, butyl, hexyl, decyl, dodecyl (lauryl), and stearate.

According to a variant, the copolymers may also include in addition to the two essential monomers, patterns of N-vinylpyrrolidone, i.e., patterns of formula (Ic).

Selection of these polymers depends on the properties which it is desired to confer on the polymers. Hence methyl methacrylate contributes a certain hardness, while lauryl methacrylate contributes suppleness and lipophile properties.

The copolymers of formula (I) have a molecular weight of between 3,000 and 100,000, preferably between 5,000 and 70,000, these molecular weights being average molecular weights by number determined by osmometry or tonometry.

The salts according to the invention appear in the form of a very strongly colored powder.

Generally, for cosmetic use the salts must have an appropriate granulometry, preferably under about 250 microns.

The present invention is also concerned with the process for preparing new acid colorant salts, this process consisting of adding to a solution of the formula (I) copolymer in an organic solvent a solution or dispersion of the acid colorant in an identical or different solvent, allowing it to act under agitation for at least 3 hours, isolating the expected salt by filtration, and washing the precipitate until the nonsalified colorant has been completely eliminated.

According to a preferred mode of realization of the process, the colorant is added in the form of a dispersion.

Among the organic solvents which can be employed in the process, we may cite ethanol, ethyl acetate, toluene, cyclohexane, acetone, butyl acetate, etc.

According to the invention, salification is done at room temperature and under strong agitation for a period of time which may vary between approximately 3 and 15 hours, and if possible sheltered from light.

Separation of the salt is preferably done by filtration on fritted glass, and the washing consists of recovering the precipitate in a certain volume of solvent, preferably ethanol and ethyl acetate.

The salt is then vacuum-dried at room temperature; the yield obtained varies between 80 and 100% of the theory.

The various analyses done on the salts obtained by the process according to the invention made it possible to show that the fixation of the colorant was achieved under excellent conditions, the percentage of unfixed colorant being less than 1%.

In order to obtain the salt in a form having a granulometry appropriate for cosmetic use, according to the invention it is possible to make use of all known means, in particular by precipitation by a non-solvent of the salt, by appropriate regulation of the agitation speed during salification or precipitation, by sharp variation in the temperature, or by grinding.

The formula (I) copolymers, as indicated above, are for the most part known and are prepared according to classic copolymerization techniques, i.e., in solution in a solvent, in mass, or in suspension in an inert liquid or in emulsion. According to the invention, polymerization in solution in a solvent was preferably used, for example in toluene, ethyl acetate, ethanol, etc.

The initiators of copolymerization are free-radical generators such as azobisisobutyronitril, peresters, or oxidoreduction systems.

The amount of the initiator is generally between 0.1 and 6% of the total weight of the monomers to be copolymerized.

The copolymerization reaction is generally effected at a temperature on the order of 30° to 85° C. for between 6 and 24 hours.

After the end of copolymerization, the copolymer is then precipitated by means of an appropriate organic solvent such as, for example, methanol, heptane, petroleum ether, etc.

When it is not possible to obtain a good precipitation by means of a solvent, another method of isolating the copolymer may consist of the formation of one of its salts, for example with oxalic acid, filtering the salt formed and then freeing the copolymer by treatment with a base such as ammonia.

The polymer is then recovered by ether, which is dry-evaporated.

The present invention is also concerned with the liquid, solid or semi-solid cosmetic compositions which, as coloring substances, contain at least one salt as defined above.

These compositions may take the form of sticks, pastes, emulsions, suspensions, dispersions or solutions and constitute lipsticks, mascaras, lip glosses, rouges, eye shadows, foundations, eye-liners, powders, or nail varnishes.

In the compositions according to the invention, the proportion of the salt is generally between 0.1 and 20% of the total weight of the composition.

The concentration depends of course on the intensity of the coloration which it is desired to confer.

According to the invention, the coloring substance in the form of a salt may be associated with mineral or organic pigments, and in particular with lacquers such as Red. No. 7 D and C calcium lacquers, Red. No. 6 and 9 D and C barium lacquers, Red No. 3 D and C and Yellow No. 5 D and C aluminum lacquers, and Orange No. 5 D and C zirconium lacquers. The Red 30 and 36 D and C may also be included in this list; because of their insolubility in water and oil these are generally considered pigments, even though they do not take the form of metallic lacquers.

Among the inorganic pigments, we may in particular cite: iron oxides (red, brown, black and yellow), chrome oxides, the ultramarines (aminosilicate polysulfides), titanium dioxide, manganese pyrophosphate, and Prussian blue (ferric ferrocyanide). These various compounds, alone or in mixture, are generally used at a concentration of between 0.1 and 40% of the total weight of the composition.

Furthermore, these compositions may also contain nacreous agents such as bismuth oxychloride, titanium, mica and guanine crystals.

When the compositions take the form of sticks, and in particular lipsticks, eye shadows, or rouges and foundations, a major share of these compositions consists of the fatty substance, which may consist of one or more waxes, and in this case the wax may be, for example: ozokerite, lanolin, lanolin alcohol, hydrogenated lanolin, acetylated lanolin, lanolin wax, beeswax, candelilla wax, microcrystalline wax, Carnauba wax, cetylic alcohol, stearylic alcohol, cocoa butter, lanoline fatty acids, petrolatum, vaselines, mono-, di- and tri-glycerides solid at 25° C., fatty esters solid at 25° C., silicone waxes such as methyloctadecaneoxypolysiloxane, and poly(-dimethylsiloxy)stearoxysiloxane, stearic monoethanolamide, colophane and its derivatives such as the glycol and glycerol abietates, hydrogenated oils solid at 25° C., the sucroglycerides and the oleates, myristates, lanolates, stearates and dihydroxystearates of calcium, magnesium, zirconium and aluminum.

The fatty substance may likewise consist of a mixture of at least one wax and at least one oil, and in this case the oil may be, for example: paraffin oil, Purcellin oil, perhydrosqualene, sweet almond oil, avocado oil, calophyllum oil, castor oil, sesame oil, jojoba oil, mineral oils having a boiling point between 310° and 410° C., silicone oils such as dimethylpolysiloxanes, linoleic alcohol, linolenic alcohol, oleic alcohol, cereal-germ oils such as wheat-germ oil, isopropyl lanolate, isopropyl palmitate, isopropyl myristate, butyl myristate, cetyl myristate, hexadecyl stearate, butyl stearate, decyl oleate, the acetyl glycerides, alcohol octanoates and decanoates and polyalcohol octanoates and decanoates such as the glycol and glycerol octanoates and decanoates, alcohol and polyalcohol ricinoleates such as cetyl ricinoleates, isostearylic alcohol, isocetyl lanolate, isopropyl adipate, hexyl laurate, and octyldodecanol.

Generally the fatty substances in these compositions in stick form may represent up to 99.9% by weight of the total weight of the composition.

These compositions may likewise contain other ingredients such as, for example, glycols, polyethyleneglycols, polypropyleneglycols, monoalkanolamides, uncolored polymers, mineral or organic fillers, preservatives, UV filters, or other additives customary in cosmetics.

These compositions in stick form are preferably anhydrous, however in some cases they may contain a certain amount of water not generally exceeding 40% of the total weight of the cosmetic composition.

When the cosmetic compositions according to the invention take the form of semi-solids (pastes or cremes), they may be either anhydrous or aqueous and constitute mascaras, eye-liners, foundations, rouges, eye shadows, lipsticks, eye-circle coverups, etc.

When these pastes or cremes are in contrast aqueous, they are then more particularly emulsions of the water-in-oil or oil-in-water type, the fatty phase of which represents from 1 to 98.8% by weight, the water phase from 1 to 98.8%, and the emulsifying agent 0.1 to 30%.

These compositions may also contain other conventional ingredients such as perfumes, antioxidizing agents, preservatives, gelling agents, UV filters, colorants, pigments, nacreous agents, uncolored polymers, and mineral or organic fillers.

When the compositions take the form of a powder, they consist essentially of a mineral or organic filler such as talc, kaolin, starches, polyethylene powders or polyamide powders, as well as additives such as binders, colorants, etc.

Such compositions may likewise contain various additives customary in cosmetics such as perfumes, antioxidizing agents, preservative agents, etc.

When these compositions according to the invention take the form of nail varnishes, they consist essentially of nitrocellulose and a natural or synthetic polymer in solution in a solvent system, this solution perhaps containing other additives such as pigments and/or nacreous agents.

According to this form of realization, the salt according to the invention is present in a proportion of between 0.1 and 5% by weight.

Several examples of preparation of the salts according to the invention as well as several examples of compositions obtained from them will now be given by way of illustration and without any limiting character whatsoever.

PREPARATION OF THE AMINO POLYMERS

Polymer A

Preparation of the methacrylate copolymer of ethyl N,N-dimethylamino-2 (25%)—methyl methacrylate (75%).

In a 1-liter balloon flask equipped with a mechanical shaker, a nitrogen lead-in and a cooling apparatus, 112.5 g of methyl methacrylate, 37.5 g of ethyl N,N-dimethylamino-2 and 2.5 g of azobisisobutyronitril in solution in 150 g of toluene are introduced.

The solution is heated while being agitated for 5 h at 80° C. After cooling, the polymer is precipitated by adding heptane.

The polymer is recovered by filtration and washing in order to eliminate the residual monomers.

The sought-after polymer is thus obtained with a yield of 82%.

The polymers B to H in the following Table I were prepared according to the same method as that described above.

TABLE I

| Monomers % by weight | Polymer B | Polymer C | Polymer D | Polymer E | Polymer F | Polymer G | Polymer H |
|---|---|---|---|---|---|---|---|
| ethyl N,N—dimethylamino-2 methacrylate | 75 | 50 | 75 | 50 | 25 | 18 | 25 |
| Lauryl methacrylate | | | 25 | 50 | 75 | | |
| Methyl methacrylate | 25 | 50 | | | | 77 | 75 |
| N—vinylpyrrolidone | | | | | | 5 | |
| Yield % | 86 | 90 | 60 | 58 | 57 | 82 | 75 |
| Precipitant | heptane | heptane | heptane | * | methanol | heptane | heptane |

*Precipitation by formation of oxalate and release of the amino copolymer by ammonia.

Polymer I

Preparation of the copolymer methacrylamide propyl N,N-dimethylamino-3 (95%)—methyl methacrylate (5%).

In a 500 ml balloon flask equipped with a mechanical shaker, a nitrogen lead-in and a cooling apparatus, 47.5 g of methacrylamide propyl N,N-dimethylamino-3, 2.5 g of methyl methacrylate, 0.5 g of azobisisobutyronitril and 100 g of ethanol are introduced. The reactive mixture is heated under agitation to 68° C. for 40 h. It is allowed to cool, then the polymer is recovered by precipitation in petroleum ether. Yield 78%.

PREPARATION OF THE SALTS

EXAMPLE 1

Preparation of the salt of the "Red 21 D and C" colorant (formula II) and the A polymer.

50 g of "Red 21 D and C" colorant is dispersed in 1.5 l of ethanol. Drop by drop and under agitation, 200 g of an ethanolic solution (and if necessary chloroform) containing 50 g of the A polymer is added. The mixture is shaken for about 15 h at room temperature and sheltered from light. It is filtered over fritted glass, and the recovered product is washed several times with ethanol and then with ethyl acetate until the unfixed colorant has been totally eliminated.

After vacuum-drying, the sought-after salt is obtained with a yield of 70%, the colorant's fixation percentage being 35.5%. By "fixation percentage" is understood the colored polymer's acid colorant content.

According to the same method as that described in example I, the salts in examples 2 to 10 in Table II were prepared.

TABLE II

| Ex. | Colorants | Polymers | Fixation % | Yield % |
| --- | --- | --- | --- | --- |
| 2 | Red 21 D and C (Formula II) | B | 45 | 72 |
| 3 | Red 21 D and C (Formula II) | C | 46 | 75 |
| 4 | Red 21 D and C (Formula II) | D | 46 | 69 |
| 5 | Red 21 D and C (Formula II) | E | 44,5 | 76 |
| 6 | Red 21 D and C (Formula II) | F | 46 | 70 |
| 7 | Red 21 D and C (Formula II) | G | 45 | 65 |
| 8 | Red 27 D and C (Formula IV) | H | 35 | 70 |
| 9 | Orange 5 D and C (Formula III) | H | 38 | 60 |
| 10 | Orange 5 D and C (Formula III) | I | 40 | 80 |

EXAMPLES OF COMPOSITION

EXAMPLE 11

A lipstick is prepared according to the invention by mixing the following ingredients:

| | |
| --- | --- |
| Microcrystalline wax | 11 g |
| Vinyl polylaurate | 20 g |
| Docosanoyl-1 (ethyl-2) hexyloxy-3 propanol-2 | 20 g |
| Liquid lanolin | 9 g |
| Castor oil | 8 g |
| Sesame oil | 10 g |
| Acetoglyceride | 9 g |
| Petrolatum oil | 5 g |
| Oleic alcohol | 5 g |
| Butylhydroxytoluene | 0.2 g |
| Polyethylene wax | 2.8 g |
| Black iron oxide | 0.2 g |
| Titanium oxide | 1.1 g |
| Yellow 5 D and C, F aluminum lacquer | 2.4 g |
| Red 7 D and C calcium lacquer | 1.45 g |
| Red 3 D and C aluminum lacquer | 5.3 g |
| Salt prepared according to Ex. 1 | 2 g |
| Perfume | 0.8 g |

EXAMPLE 12

A lipstick is prepared according to the invention by mixing the following ingredients:

| | |
| --- | --- |
| Hard microcrystalline wax | 10 g |
| Isopropyl lanolate | 6 g |
| Lanolin alcohol | 6 g |
| Soft microcrystalline wax | 10 g |
| Myristyl lactate | 8 g |
| Liquid lanolin | 10 g |
| Polybutene | 20 g |
| Sesame oil | 10 g |
| Castor oil | 10 g |
| Oleic alcohol | 7.9 g |
| Petrolatum oil | 2 g |
| Butylhydroxytoluene | 0.1 g |
| Brown iron oxide | 2.7 g |
| Red 7 D and C calcium lacquer | 0.18 g |
| Red 8 D and C (sodium salt) | 1.26 g |
| Red 3 D and C aluminum lacquer | 5.10 g |
| Titanium oxide | 1.10 g |
| Salt prepared according to Ex. 3 | 2 g |
| Perfume | 0.6 g |

EXAMPLE 13

A lip gloss is prepared according to the invention by mixing the following ingredients:

| | |
| --- | --- |
| Vinyl acetate - Allyl stearate 35/65 copolymer | 5 g |
| Vinyl polylaurate | 20 g |
| Docosanoyl-1 (ethyl-2) hexyloxy-3 propanol-2 | 20 g |
| Polyethylene wax | 15 g |
| Mineral oil | 12 g |
| Sesame oil | 8 g |
| Oleic alcohol | 3 g |
| Butylhydroxytoluene | 0.1 g |
| Butyl para-hydroxybenzoate | 0.2 g |
| Polyethylene wax | 2 g |
| Liquid lanolin | 14.7 g |
| Titanium oxide | 0.1 g |
| Red 36 D and C | 1.1 g |
| Red 30 D and C | 0.2 g |
| Salt prepared according to Ex. 4 | 0.5 g |
| Perfume | 0.2 g |

EXAMPLE 14

A rouge is prepared according to the invention in the form of a compact powder by mixing the following ingredients:

| | |
| --- | --- |
| Talc | 41.64 g |
| Starch | 10 g |
| Zinc stearate | 2 g |
| Bismuth oxychloride | 10 g |
| Castor oil | 0.7 g |
| Petrolatum oil | 3.5 g |
| Isopropyl myristate | 0.5 g |

-continued

| Oleic alcohol | 0.6 g |
|---|---|
| Phytosterol | 0.3 g |
| Polypeptide oleate | 0.3 g |
| Butyl hydroxyanisole | 0.01 g |
| Magnesium carbonate | 0.55 g |
| Magnesium violet | 7 g |
| Iron oxide | 2 g |
| Titanium mica | 20 g |
| Salt prepared according to Ex. 3 | 0.5 g |
| Perfume | 0.4 g |

EXAMPLE 15

A composition in the form of a powder is prepared according to the invention by mixing the following ingredients:

| Talc | 77.5 g |
|---|---|
| Zinc oxide | 23.8 g |
| Zinc stearate | 2.1 g |
| Salt prepared according to Ex. 8 | 0.3 g |
| D and C Yellow 5 aluminum lacquer | 0.7 g |
| Perfume | 1.1 g |

EXAMPLE 16

A composition called "tracer-liner" is prepared according to the invention by mixing the following ingredients:

| Stearic acid | 1 g |
|---|---|
| Hydrogenated castor oil | 3 g |
| Triethanolamine | 0.4 g |
| Propyl methylhydroxy cellulose | 2.5 g |
| Polyethylene glycol monostearate | 12 g |
| Methyl parahydroxy benzoate | 0.1 g |
| Propyl parahydroxy benzoate | 0.1 g |
| Ethyl parahydroxy benzoate | 0.1 g |
| Silicates with high Mg content | 0.5 g |
| Titanium dioxide | 10 g |
| Ultramarine blue | 0.8 g |
| Salt prepared according to Ex. 5 | 0.3 g |
| Black iron oxide | 2 g |
| Suff. quant. sterile permuted water | 100 g |

EXAMPLE 17

A rouge is prepared according to the invention in the form of an oil-in-water emulsion by mixing the following ingredients:

| Stearic acid | 2.5 g |
|---|---|
| Sorbitan monostearate polyoxyethylenated with 20 moles of ethylene oxide | 0.5 g |
| Petrolatum oil | 10 g |
| Triethanolamine | 1 g |
| Sorbitol | 5 g |
| Silicates with high Mg content | 3 g |
| Titanium dioxide | 3 g |
| Black iron oxide | 0.1 g |
| Yellow iron oxide | 3 g |
| Salt prepared according to Ex. 8 | 2 g |
| Titanium mica | 5 g |
| Methyl parahydroxy benzoate | 0.2 g |
| Propyl parahydroxy benzoate | 0.150 g |
| Suff. quant. sterile permuted water | 100 g |

EXAMPLE 18

A foundation is prepared according to the invention by mixing the following ingredients:

| Stearic acid | 5.5 g |
|---|---|
| Cetylic alcohol | 1.2 g |
| Decyl oleate | 12.8 g |
| Petrolatum oil | 6.1 g |
| Polyethylene glycol stearate | 0.7 g |
| 2,4,4' trichloro-2' hydroxy-biphenyl ether | 0.15 g |
| Saturated fatty acid triglyceride $C_{10}$–$C_{18}$ | 3.6 g |
| Propylene glycol | 4 g |
| Triethanolamine | 1 g |
| Sterile permuted water | 84.65 g |
| Methyl parahydroxy benzoate | 0.2 g |
| Propyl parahydroxy benzoate | 0.1 g |
| Yellow iron oxide | 1 g |
| Salt prepared according to Ex. 12 | 0.8 g |
| Black iron oxide | 0.2 g |
| Rutilated titanium dioxide | 8 g |

EXAMPLE 19

A nail varnish is prepared according to the invention by mixing the following ingredients:

| ½ second nitrocellulose | 12 g |
|---|---|
| Arylsulfonamide formaldehyde copolymer | 8 g |
| Camphor | 2 g |
| Butyl phthalate | 4 g |
| Ethyl acetate | 10 g |
| Toluene | 20 g |
| Ethyl alcohol | 3 g |
| Butyl alcohol | 3 g |
| Butyl acetate | 38 g |
| Bentone 27 | 1 g |
| Phosphoric acid | 0.01 g |
| Titanium oxide | 0.5 g |
| Yellow 5 D and C zirconium lacquer | 0.5 g |
| Brown iron oxide | 0.3 g |
| Salt prepared according to Ex. 10 | 0.7 g |

EXAMPLE 20

An eye shadow is prepared according to the invention in the form of a water-in-oil emulsion by mixing the following ingredients:

| Saturated fatty acid and sorbitan ester | 4 g |
|---|---|
| Microcrystalline wax | 5 g |
| Beeswax | 2 g |
| Paraffin oil | 8 g |
| Methyl parahydroxy benzoate | 0.3 g |
| Titanium mica pigment | 10 g |
| Polyethylene powder | 4.5 g |
| Salt prepared according to example 9 | 0.5 g |
| Suff. quant. sterile permuted water | 100 g |

EXAMPLE 21

A mascara is prepared according to the invention by mixing the following ingredients:

| Carnauba wax | 10 g |
|---|---|
| Ceresine | 9 g |
| Triethanolamine stearate | 12 g |
| Hydroxyethyl cellulose | 2 g |
| Black iron oxide | 10 g |
| Methyl parahydroxy benzoate | 0.3 g |
| Sodium mercurithiolate | 0.002 g |
| Salt prepared according to Ex. 1 | 1 g |
| Suff. quant. demineralized water | 100 g |

EXAMPLE 22

An anhydrous foundation is prepared according to the invention in the form of a stick by mixing the following ingredients:

| | |
|---|---|
| Carnauba wax | 6 g |
| Paraffin oil | 22 g |
| Isopropyl lanolate | 4 g |
| Isopropyl myristate | 33.15 g |
| Isononyl isononanoate | 6 g |
| Propyl parahydroxy benzoate | 0.1 g |
| Magnesium carbonate | 6 g |
| Talc | 12 g |
| Titanium bioxide | 9 g |
| Yellow iron oxide | 0.9 g |
| Black iron oxide | 0.25 g |
| Salt prepared according to Ex. 6 | 0.4 g |
| Perfume | 0.2 g |
| | 100 g |

EXAMPLE 23

An eye shadow is prepared according to the invention in the form of a compacted powder by mixing the following ingredients:

| | |
|---|---|
| Talc | 14.99 g |
| Manganese violet | 15 g |
| Salt prepared according to Ex. 7 | 7 g |
| Iron oxide | 3 g |
| Bismuth oxychloride | 10 g |
| Micas | 15 g |
| Titanium dioxide | 17 g |
| Cochineal carmine | 3 g |
| Petrolatum oil | 8.7 g |
| Isopropyl myristate | 1.2 g |
| Oleic alcohol | 1.5 g |
| Phytosterol | 0.9 g |
| Polypeptide oleate | 0.9 g |
| Castor oil | 1.8 g |
| Butyl hydroxanysole | 0.01 g |
| | 100 g |

We claim:

1. An acid colorant salt of an acid colorant salified by a copolymer having a tertiary amine function, said acid colorant being selected from the group consisting of Red 21 D and C, Orange 5 D and C, Red 27 D and C, Orange 10 D and C, Red 3 D and C, Acid Red 7 D and C, Red 2 D and C, Red 4 D and C, Acid Red 8 D and C, Acid Red 33 D and C, Acid Yellow 5 D and C, Acid Yellow 6 D and C, Acid Green 5 D and C, Acid Yellow 10 D and C, Acid Green 3 D and C, Blue 1 D and C, Blue 2 D and C and Violet 1 D and C, and said copolymer having the formula

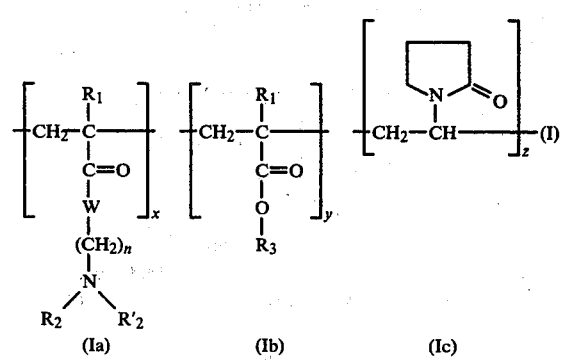

wherein
n is 2 or 3,
W represents a bond, —O— or —NH—,
$R_1$ represents H or —$CH_3$,
$R_2$ and $R_2'$ each independently represent lower alkyl having from 1 to 3 carbon atoms,
$R_3$ represents linear or branched alkyl having from 1 to 18 carbon atoms,
x represents from 5 to 95 weight percent,
y represents from 5 to 95 weight percent, and
z represents from 0 to 20 weight percent, with x+y+z being equal to 100 weight percent.

2. The acid colorant salt of claim 1 wherein the (Ia) unit is derived from the polymerization of a monomer which is ethyl N,N-dimethylamino-2, ethyl N,N-diethylamino-2, propyl N,N-dimethylamino-3 and propyl N,N-diethylamino-3 acrylates or methacrylates; and ethyl N,N-dimethylamino-2, ethyl N,N-diethylamino-2, propyl N,N-dimethylamino-3 and propyl N,N-diethylamino-3 acrylamides or methacrylamides.

3. The acid colorant salt of claim 1 wherein the (Ib) unit is derived from the polymerization of a monomer which is methyl, ethyl, propyl, butyl, hexyl, decyl, dodecyl and stearyl acrylates or methacrylates.

4. The acid colorant salt of claim 1 wherein said polymer has a molecular weight ranging from 3,000 to 100,000.

5. The acid colorant salt of claim 1 wherein said polymer has a molecular weight ranging from 5,000 to 70,000.

6. In a cosmetic composition, in liquid, semi-solid or solid form, containing a coloring substance, the improvement comprising, as said coloring substance, the acid colorant salt of claim 1.

7. The cosmetic composition of claim 6 wherein said coloring substance is present in an amount ranging from 0.1 to 20 percent by weight, based on the total weight of said composition.

8. The cosmetic composition of claim 6 which also contains at least one of an inorganic or organic filler, present in an amount ranging from 0.1 to 40 percent by weight, based on the total weight of said composition.

9. The cosmetic composition of claim 6 which also contains an effective amount of a nacreous agent selected from bismuth oxychloride, titanium mica or guanine crystals.

10. The cosmetic composition of claim 6, in the form of a stick containing up to 99.9 percent by weight of, as a fatty substance, at least one cosmetically acceptable wax.

11. The cosmetic composition of claim 10 wherein said fatty substance also includes an effective amount of at least one cosmetically acceptable oil.

12. The cosmetic composition of claim 10 which also contains up to 40 weight percent water, based on the total weight of said composition.

13. The cosmetic composition of claim 6 in the form of an anhydrous or aqueous paste or cream.

14. The cosmetic composition of claim 1 in the form of a water-in-oil or oil-in-water emulsion, wherein the oil phase comprises 1 to 98.8 percent by weight thereof, the water phase comprises from 1 to 98.8 percent by weight thereof, and an emulsifying agent present in an amount ranging from 0.1 to 30 percent by weight, based on the total weight of said composition.

15. The cosmetic composition of claim 6 in the form of a compact or free powder, said composition containing, as a filler, an effective amount of at least one of talc, kaolin, starch, polyethylene powder or polyamide powder.

16. The cosmetic composition of claim 6 in the form of a nail varnish, said composition containing from 0.1 to 5 percent by weight of said coloring substance in a nail varnish base.

* * * * *